United States Patent [19]
Del Rossi et al.

[11] Patent Number: 5,324,699
[45] Date of Patent: Jun. 28, 1994

[54] ALKYLATION CATALYST COMPLEX

[75] Inventors: Kenneth J. Del Rossi, Woodbury, N.J.; Albin Huss, Jr., Chadds Ford, Pa.; Samuel A. Tabak, Wenonah, N.J.

[73] Assignee: Mobil Oil Corporation, Fairfax, Va.

[21] Appl. No.: 900,517

[22] Filed: Jun. 17, 1992

Related U.S. Application Data

[63] Continuation of Ser. No. 608,763, Nov. 5, 1990, abandoned.

[51] Int. Cl.$^5$ .............................................. B01J 31/00
[52] U.S. Cl. ................................... 502/162; 502/150; 502/168; 568/2
[58] Field of Search .................... 502/150, 162, 168; 568/2

[56] References Cited

U.S. PATENT DOCUMENTS

| | | | |
|---|---|---|---|
| 2,296,370 | 9/1942 | Slotterbeck | 196/10 |
| 2,296,371 | 9/1942 | Slotterbeck | 196/10 |
| 2,345,095 | 3/1944 | Bruner et al. | 260/683.4 |
| 2,469,335 | 5/1949 | Johnson | 502/203 |
| 2,557,113 | 6/1951 | Kennedy | 502/150 |
| 2,981,772 | 4/1961 | Holzman | 502/150 |
| 3,873,634 | 3/1975 | Hoffman | 260/683.44 |
| 3,925,500 | 12/1975 | Wentzheimer | 260/683.44 |
| 4,795,728 | 1/1989 | Kocal | 502/162 |

FOREIGN PATENT DOCUMENTS

| | | |
|---|---|---|
| 545441 | 8/1939 | United Kingdom . |
| 550711 | 8/1940 | United Kingdom . |

OTHER PUBLICATIONS

L. F. Albright et al., "Alkylation of Isobutane with $C_4$ Olefins", 27 Ind. Eng. Chem. Res., 381–397, (1988).
22 Kirk-Othmer Encyclopedia of Chemical Technology, 3rd ed., 332 (1983).

*Primary Examiner*—Patrick P. Garvin
*Assistant Examiner*—E. D. Irzinski
*Attorney, Agent, or Firm*—Alexander J. McKillop; Dennis P. Santini; Robert B. Furr, Jr.

[57] ABSTRACT

The present invention relates to a novel alkylation catalyst complex and to alkylation processes employing such a catalyst complex. More specifically, the invention relates to a novel catalyst complex comprising a $BF_3:H_3PO_4$ adduct, and at least one polar hydrocarbon formed in situ. The catalyst complex may optionally include water as well as an added solubilizing agent. The invention further includes a pretreatment method for enhancing the isoparaffin selectivity of a catalyst complex containing a $BF_3:H_3PO_4$ adduct.

11 Claims, 1 Drawing Sheet

ALKYLATION CATALYST COMPLEX

This is a continuation of Ser. No. 608,763 filed on Nov. 5, 1990, now abandoned.

FIELD OF THE INVENTION

The present invention relates to a novel alkylation catalyst and to alkylation processes employing such a catalyst. More specifically, the invention relates to a novel catalyst comprising a $BF_3:H_3PO_4$ adduct, and at least one polar compound formed in situ. The catalyst may optionally include water as well as an added solubilizing agent. The invention further includes a pretreatment method for enhancing the isoparaffin selectivity of a catalyst containing a $BF_3:H_3PO_4$ adduct.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is preferably maintained at 88 to 94 weight percent by the continuous addition of fresh acid and the continuous withdrawal of spent acid. The hydrofluoric acid process is less temperature sensitive and the acid is easily recovered and purified.

Both sulfuric acid and hydrofluoric acid alkylation share inherent drawbacks including environmental and safety concerns, acid consumption, and sludge disposal. Research efforts have been directed to developing alkylation catalysts which are equally as effective as sulfuric or hydrofluoric acids but which avoid many of the problems associated with these two acids.

For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). The second in this series of articles discusses the byproduct conjunct polymers which appear to promote sulfuric acid alkylation at concentrations up to about 4 to 5 percent, but impede alkylation at higher concentrations. The conjunct polymers are believed to contain $C_5$ and $C_6$ ring groups, and are highly unsaturated. See Albright et al. at 386, column 1.

Catalysts comprising $BF_3$ as well as $BF_3:H_3PO_4$ adducts have been proposed, and are discussed in greater detail below. While these catalysts effectively overcome the safety and environmental drawbacks of sulfuric and hydrofluoric acid alkylation systems, the volume and quality of $BF_3$ alkylates have not, in the past, proven comparable to that of sulfuric or hydrofluoric acid alkylates.

U.K. Patent 545,441, assigned to Standard Oil Development Company, teaches a $BF_3:H_3PO_4$ catalyzed isoparaffin-olefin alkylation process.

U.S. Pat. No. 2,345,095 to Bruner teaches a paraffin-olefin alkylation process catalyzed by a boron trifluoride-water complex, represented by the formula $BF_3:nH_2O$, where n is preferably from 1 to 1.5.

U.S. Pat. Nos. 2,296,370 and 2,296,371 to Slotterbeck disclose a $BF_3:H_2O:HF$ catalyst system and an isoparaffin-olefin alkylation process employing the same. The catalyst system is said to avoid yield loss due to oxidation of the resulting alkylate product.

U.K. Patent 550,711 teaches a process for increasing the activity of at least partially spent $BF_3:H_2O$ catalyst systems for reuse in an organic condensation reaction. Briefly, the process volatilizes $BF_3$ from the liquid catalyst mass to the extent required to promote separation of a distinct hydrocarbon phase from the catalyst mass. This hydrocarbon phase is then decanted off and fresh $BF_3$ is added to restore catalytic activity.

Canadian Patent 424,000 teaches a process for producing gasoline boiling range hydrocarbons from isobutane and a normally gaseous olefin by absorbing the olefin in phosphoric acid of at least 75 weight percent concentration with an amount of isobutane equal to at least three moles of isobutane per mole of alkyl phosphate in the presence of a catalytic mixture of phosphoric acid and boron halide at temperature between 20° C. and 60° C.

U.S. Pat. No. 3,873,634 to Hoffman teaches a method of increasing the rate of ethylene alkylation by isobutane by carrying out the reaction simultaneously with the alkylation of a small amount of a higher weight olefin is isobutane in the presence of a $BF_3:H_3PO_4$ catalyst complex at low temperature and pressure.

U.S. Pat. No. 3,925,500 to Wentzheimer discloses a combined acid alkylation and thermal cracking process employing a $BF_3:H_3PO_4$ acid catalyst in which unconverted propane and ethane from the alkylation process are converted, for example, to propylene and ethylene which are subsequently alkylated with isobutane to evolve a valuable liquid fuel.

U.S. Pat. No. 4,795,728 to Kocal teaches a hydrofluoric acid catalyzed alkylation process for producing motor fuel. The hydrofluoric acid catalyst complex includes from 0.5 to 5 weight percent of a cationic or anionic surfactant component enabling the process to be operated at an olefin:acid volumetric feed ratio of greater than 1.0 while maintaining acceptable alkylate quality.

SUMMARY OF THE INVENTION

The present invention provides an improved alkylation catalyst and an isoparaffin/olefin alkylation process employing the same. It has unexpectedly been found in accordance with the invention that alkylation in the presence of a catalyst containing a $BF_3:H_3PO_4$ adduct evolves certain byproducts which improve alkylation selectivity when allowed to accumulate in contact with the catalyst. Thus, while in previously known isoparaffin:olefin alkylation processes, it has been desirable and in fact absolutely necessary to avoid accumulation of alkylation byproducts in the alkylation reaction zone, buildup of certain byproducts from $BF_3:H_3PO_4$ alkylation surprisingly improves isoparaffin:olefin alkylation selectivity and continues to improve selectivity to an even greater extent as byproduct is allowed to accumulate in the alkylation reaction zone.

The invention provides an acid catalyst complex for liquid phase alkylation of an isoparaffin with an olefin comprising a $BF_3:H_3PO_4$ adduct together with a polar compound formed in situ by the reaction of said olefin with $H_3PO_4$.

The invention also includes, in a first process aspect, a continuous alkylation process for producing high octane gasoline comprising effecting reaction of an isoparaffin containing from 4 to 20 carbon atoms with an olefin containing from 2 to 12 carbon atoms at from about −40° C. to about 200° C. and at a pressure in the range of subatmospheric to about 5000 psig by contacting a mixture of isoparaffin and olefin with a catalyst complex comprising a $BF_3:H_3PO_4$ adduct together with a polar compound formed in situ.

The invention further includes, in a second process aspect, a continuous alkylation process for producing high octane gasoline comprising:

(a) providing an alkylation reaction zone;

(b) effecting reaction of an isoparaffin containing from 4 to 20 carbon atoms with an olefin having from 2 to 12 carbon atoms within said alkylation reaction zone at temperature from about −40° C. to about 200° C. and at a pressure in the range of subatmospheric to about 5000 psig by contacting a mixture of isoparaffin and olefin with a catalyst complex comprising from about 4 to about 65 weight percent $BF_3$, from about 2 to about 60 weight percent $H_3PO_4$, up to about 15 weight percent $H_2O$, and from about 0.1 to about 90 weight percent of a polar byproduct formed in situ to evolve a gasoline boiling range alkylate product; and (b) withdrawing said alkylate product and accumulating a concentration of said polar hydrocarbon byproduct within said alkylation reaction zone sufficient to improve alkylate yield by recycling at least a portion of said polar hydrocarbon byproduct to said alkylation reaction zone.

The present invention still further includes, a pretreatment method improving the isoparaffin selectivity of an isoparaffin:olefin alkylation catalyst complex containing a $BF_3:H_3PO_4$ adduct, said pretreatment method comprising reacting said $BF_3:H_3PO_4$ adduct with an olefin-rich feedstock to produce a polar hydrocarbon byproduct in situ and retaining at least a portion of said polar hydrocarbon byproduct in contact with with said catalyst complex.

DESCRIPTION OF THE DRAWING

The FIGURE is a simplified schematic diagram illustrating the major processing steps of the present invention.

DETAILED DESCRIPTION

Feedstocks

Figure 1:
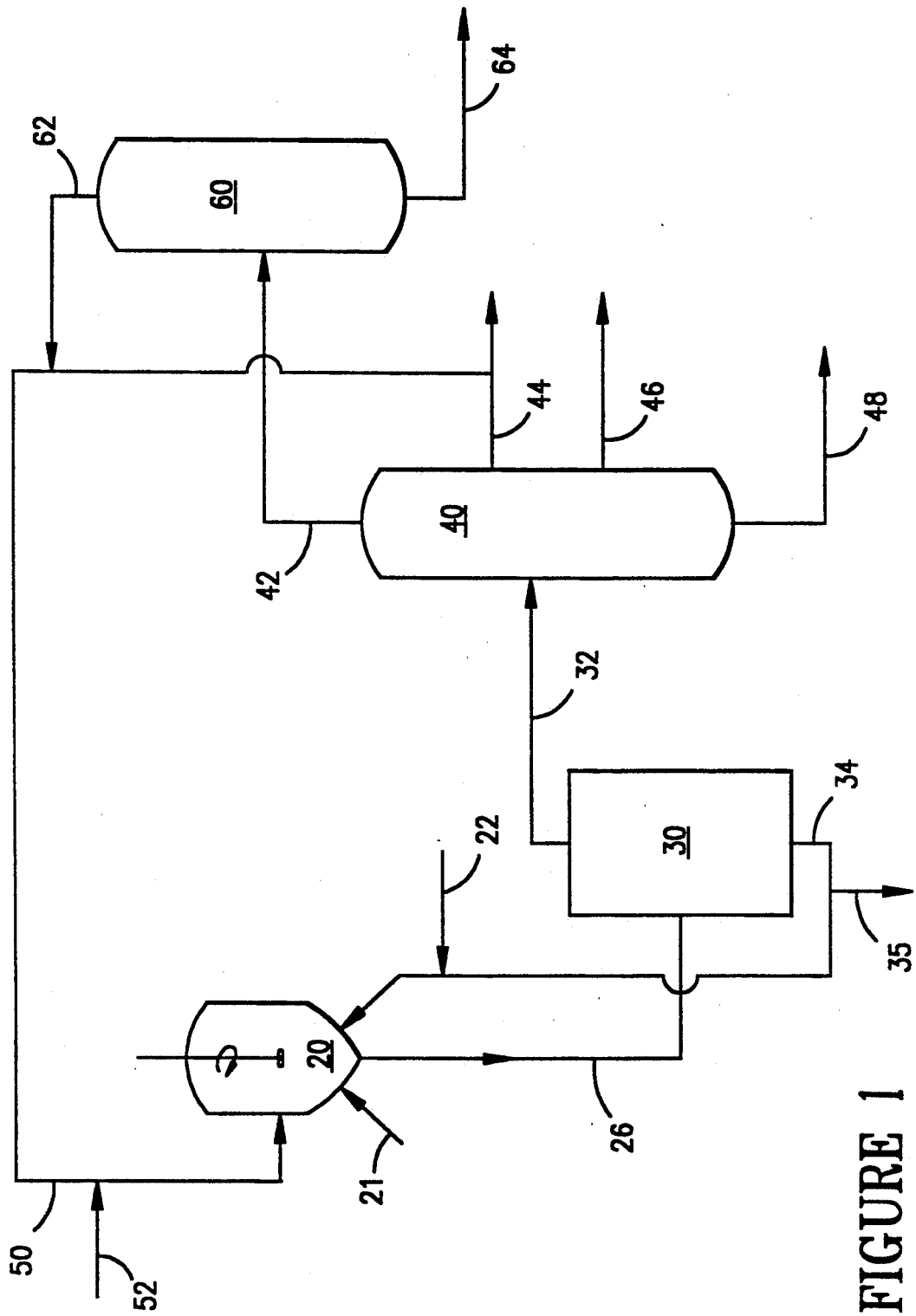

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The most preferred olefins include the $C_4$ olefins, for example, butene-1, butene-2, isobutylene, or a mixture of one or more of these $C_4$ olefins. Suitable feedstocks for the process of the present invention are described in U.S. Pat. No. 3,862,258 to Huang et al. at column 3, lines 44-56, the disclosure of which is incorporated by reference as if set forth at length herein.

The overall molar ratio of isoparaffin to olefin in the reactor feed during normal alkylation operation is generally between 1:1 and 100:1, preferably between about 5:1 and about 20:1. Upon process startup with fresh catalyst, the catalyst complex may optionally be pretreated with an olefin-rich feedstock to improve initial isoparaffin selectivity. Under these optional startup conditions, the most preferred feedstock contains at least 50 mole percent olefins.

Process Conditions

The present alkylation process is suitably conducted at temperatures of from about −40° C. to about 200° C., preferably below about 40° C. to avoid undesirable side reactions, and most preferably from about 0° C. to about 20° C. Lower reaction temperatures are preferred to maximize alkylate octane. However, upon process startup with fresh catalyst, higher temperatures in the range of about 30° C. to about 100° C. may optionally be used to promote accumulation of polar byproducts.

Operating pressure is controlled to maintain the reactants in the liquid phase, and is suitably from about 50 to about 5000 psig, preferably from about 50 to about 1500 psig, and more preferably from about 80 to about 200 psig.

The particular operating conditions used in the present process will depend on the specific alkylation reaction, and will vary within the disclosed ranges depending upon the available feedstock and the desired alkylate quality. Process conditions such as temperature, pressure, space velocity and molar ratio of the reactants will effect the characteristics of the resulting alkylate, and may be adjusted within the disclosed ranges by those skilled in the art with only minimal trial and error.

The process can be carried out in a continuous stirred tank reactor such as that employed in sulfuric acid alkylation or in a tubular riser type reactor such as used for hydrofluoric acid alkylation.

Catalyst Alkylation

The catalyst of the present invention comprises from about 4 to about 65 weight percent $BF_3$, from about 2 to about 60 weight percent $H_3PO_4$, up to about 15 weight percent $H_2O$, together with polar compounds formed in situ, and optionally an added solubilizing agent. The total concentration of polar compounds formed in situ may range from about 0.1 to about 90 percent by weight of the catalyst. The catalyst complex preferably comprises from about 24 to about 55 weight percent $BF_3$, and from about 23 to about 60 weight percent $H_3PO_4$ together with a total concentration of polar compounds formed in situ and added solubilizing agent of up to about 40 weight percent.

Solubilizing Agent

The catalyst may optionally include an added solubilizing agent. For a general discussion of the characteristics of suitable solubilizing agents, see 22 *Kirk-Othmer Encyclopedia of Chemical Technology*, 3rd ed., 332 (1983), which is incorporated by reference as if set forth at length herein. Non-limiting examples of suitable solubilizing agents include sulfonic and phosphonic compounds, for instance, sulfated esters, sulfated alkanolamides, alkyl sulfates, sulfonates containing aliphatic, aromatic, alkylaromatic or naphthenic constituents, alkylphosphates, alkylpolyphosphates, phosphate mono-esters, phosphate di-esters, and phosphate tri-esters. Anionic and cationic surfactants are also useful solubilizing agents in the present invention.

Process Flow

The process of the present invention is suitably carried out in a stirred tank reactor. The liquid mixture from the continuous stirred tank reactor is piped to a liquid-liquid separator, for example, a decanter, where the more dense liquid alkylation catalyst rapidly migrates to the bottom of the settler, while the gasoline product floats to the top of the settler. The liquid catalyst is withdrawn from the bottom of the settler, and may be disposed and/or combined with fresh catalyst and sent back to the reactor. The gasoline product is collected from the top of the settler and piped to a $BF_3$ stripper. The gasoline product may be scrubbed with an aqueous caustic solution (NaOH) to remove residual acid, while the excess $BF_3$ gas recovered in the stripper is recycled back to the reactor.

Referring now to the FIGURE, one embodiment of the present invention is schematically illustrated in which a continuous alkylation process is conducted in the presence of a catalyst comprising a $BF_3$:$H_3PO_4$ adduct in a stirred tank reactor containing a well stirred emulsion of reactants and catalyst. The alkylation reaction of the present invention proceeds under anhydrous conditions, however, water may optionally be present in the reaction zone at concentrations up to about 15 weight percent of the total catalyst.

Isoparaffin, e.g. isobutane, containing recycled $BF_3$ is mixed with makeup $BF_3$ from line 52 and charged through line 50 to stirred tank reactor 20. Mixed isobutane:olefin feed and fresh phosphoric acid catalyst are also added to the stirred tank reactor through lines 21 and 22, respectively, to provide an effective weight hourly space velocity (WHSV) of about 0.5 $hr^{-1}$. The total recycle and makeup $BF_3$ charge rate is controlled to maintain the concentration of $BF_3$ in the catalyst complex of from about 30 to about 65 weight percent based on the total weight of the catalyst present in the reaction zone.

The relative flowrates of isoparaffin and olefin are controlled to maintain an isoparaffin:olefin ratio of about 10:1 in the overall feed to the stirred tank reactor. Alkylate product and spent catalyst are withdrawn from stirred tank reactor 20 through line 26. The mixture of alkylate product and spent catalyst is charged to a decanter 30 where the mixture readily separates into a lower, more dense catalyst layer and an upper, less dense, alkylate layer. The liquid catalyst is withdrawn from the bottom of the decanter 30 via line 34 and is recycled to reactor 20. A portion of the liquid catalyst is also withdrawn via line 35 for regeneration or is outhauled for suitable disposal. Flow through line 35 is controlled to maintain concentration of polar compounds in the reaction zone within the desired range of about 0.1 to about 90 weight percent of the catalyst.

The alkylate product withdrawn from decanter 30 via line 32 is charged to distillation column 40 to separate $C_5+$ alkylate from n-butane, isobutane, and $BF_3$. The overhead product from distillation column 40, enriched in propane and $BF_3$, is withdrawn from an upper section of the distillation column 40 through line 42 and is charged to $BF_3$/propane fractionator 60. The overhead stream rich in $BF_3$ is recycled to line 50 via line 62 while the bottom stream, enriched in propane, is routed through line 64 for storage, further processing downstream or resale. A side draw rich in isobutane is withdrawn from distillation column 40 through line 44 and may be partially or totally recycled to the reactor 20 via line 50 or may be partially removed from the process through line 44. A second side draw rich in normal butane is withdrawn from fractionation tower 40 through line 46 for storage, further downstream processing or resale.

EXAMPLE 1

The $BF_3$:phosphoric acid component of the catalyst of the present invention was prepared by saturating commercial phosphoric acid (Baker Chemical Company) with $BF_3$ gas (Matheson Chemical Company). The liquid catalyst was evaluated for paraffin alkylation in a continuous stirred tank reactor in accordance with the following procedure. The liquid catalyst was loaded (43.5 grams) into a 300 cc continuous stirred tank reactor. The reactor was charged with 300 cc of isobutane and pressurized to 150 psi. The reactor was then cooled to 50° F. and stirred at 1000 rpm. A pre-mixed isobutane/2-butene feed having an isobutane:2-butene weight ratio of 10:1 was then introduced to the reactor at a rate of 140 grams per hour. Gaseous $BF_3$ was also fed at a rate of 0.75 grams per hour. The liquid product from the reactor was collected in a product receiver chilled to 32° F. The off-gas from the product receiver was passed through sodium hydroxide scrubbers to remove $BF_3$, and finally through a wet test meter. The total product distribution was determined from GC analyses of liquid and off-gas samples. Results are shown below in Table 1.

TABLE 1

| (Liquid $BF_3$:$H_3PO_4$:$H_2O$ Catalyst) | | | |
|---|---|---|---|
| Hours on Stream | 168 | 175 | 192 |
| Feed I-$C_4$/2-$C_4^=$ Weight Ratio | 10 | 10 | 5 |
| Stir Rate (RPM) | 1000 | 1500 | 1500 |
| WHSV Based on Olefin, $hr^{-1}$ | 0.30 | 0.30 | 0.52 |
| Olefin Conversion, % | 90.6 | 99.8 | 99.9 |
| Yield | 1.9 | 1.8 | 2.1 |
| (Grams $C_5+$ Alkylate/ | | | |
| Gram Olefin Converted) | | | |
| Product Distribution in $C_5+$, wt. % | | | |
| $C_5$-$C_7$ | 9.6 | 11.3 | 14.0 |
| $C_8$'s | 78.3 | 78.4 | 64.1 |
| $C_9+$ | 12.1 | 10.2 | 21.9 |
| Ratio of Trimethylpentanes/ Dimethylhexanes in $C_8$'s | 6.2 | 6.1 | 5.2 |

The $BF_3$:phosphoric acid component of the catalyst of the present invention gave a near-theoretical yield of alkylate from 10:1 and 5:1 isobutane:2-butene feeds at 90+% conversion of 2-butene. With a 10:1 isobutane:2-butene feed, the alkylate product was substantially paraffinic (as evidenced by bromine numbers less than 4) and contained roughly 78 wt. % $C_8$ paraffins, 11 wt.% $C_5$-$C_7$ paraffins, and 11 wt. % $C_9+$ paraffins. The ratio of high octane trimethylpentanes to lower octane dimethylhexanes (TMP/DMH) in the $C_8$ fraction was 6.2. With a 5:1 isobutane:2-butene feed, the alkylate product contained roughly 64 wt. % $C_8$ paraffins, 14 wt. % $C_5$-$C_7$ paraffins, and 22 wt. % $C_9+$ paraffins and olefins. The ratio of high octane trimethylpentanes to lower octane dimethylhexanes (TMP/DMH) in the $C_8$ fraction was 5.2, compared with 6.2 for the 10:1 feed isobutane:2-butene.

EXAMPLE 2

A commercial $BF_3$:phosphoric acid catalyst (Englehard Minerals and Chemicals Corporation) containing 41 wt. % $BF_3$ and 59 wt. % $H_3PO_4$ was also evaluated with 10:1 and 5:1 isobutane:2-butene feeds in the 300 cc continuous stirred tank reactor described above in Example 1. The procedure and conditions for the test runs of Example 2 were identical to those stated above for Example 1. Results are shown below in Table 2.

TABLE 2

| (Anhydrous $BF_3$:$H_3PO_4$ Catalyst) | | |
|---|---|---|
| Hours on Stream | 41 | 205 |
| Feed I-$C_4$/2-$C_4$= Weight Ratio | 5 | 10 |
| Stir Rate (RPM) | 1000 | 1000 |
| WHSV Based on Olefin, hr$^{-1}$ | 0.52 | 0.30 |
| Olefin Conversion, % | 96.7 | 93.1 |
| Yield | 1.7 | 1.3 |
| (Grams $C_5$+ Alkylate/ Gram Olefin Converted) | | |
| Product Distribution in $C_5$+, wt. % | | |
| $C_5$-$C_7$ | 13.8 | 9.6 |
| $C_8$'s | 48.9 | 45.2 |
| $C_9$+ | 37.3 | 45.3 |
| Ratio of Trimethylpentanes/ Dimethylhexanes in $C_8$'s | 5.5 | 4.7 |

The anhydrous catalyst produced only 1.3 grams of alkylate per gram of 2-butene with a 10:1 isobutane:2-butene feed compared to a yield of 1.9 for the liquid catalyst of the present invention without added solubilizing agent. Furthermore, the alkylate product was highly olefinic and contained 45 wt. % $C_9$+ product. In general, the anhydrous $BF_3$:phosphoric acid catalyst was found to be less active and less selective for paraffin alkylation when compared to the $BF_3$:$H_3PO_4$:$H_2O$ catalyst of the present invention under identical conditions.

EXAMPLE 3

The following Example demonstrates the benefit of accumulating polar byproduct in contact with the $BF_3$:$H_3PO_4$:$H_2O$ catalyst. Data were obtained for both fresh and equilibrium $BF_3$:$H_3PO_4$:$H_2O$ catalysts. As noted above in Example 1, the fresh $BF_3$:$H_3PO_4$:$H_2O$ catalyst contains approximately 54 wt. % $BF_3$, 39 wt. % $H_3PO_4$ and 7 wt. % $H_2O$. An equilibrium $BF_3$:$H_3PO_4$:$H_2O$ catalyst (150 hours on-stream) was found to contain roughly 37 wt. % $BF_3$, 27 wt. % $H_3PO_4$, 5 wt. % $H_2O$, and 31 wt. % polar compounds having the boiling point distribution shown below in Table 3.

TABLE 3

| Wt. % | Cutpoint |
|---|---|
| 5 | 359° F. |
| 10 | 392 |
| 20 | 443 |
| 50 | 583 |
| 60 | 643 |
| 80 | 785 |
| 95 | 945 |

Results from continuous operation with the $BF_3$:$H_3PO_4$:$H_2O$ catalyst after 72 and 168 hours on-stream (HOS) with a 10:1 isobutane:2-butene feed are shown below in Table 4.

TABLE 4

| (Liquid $BF_3$:$H_3PO_4$:$H_2O$ Catalyst) | | |
|---|---|---|
| Hours on Stream | 72 | 168 |
| Feed I-$C_4$/2-$C_4$= Ratio | 5 | 10 |
| Stir Rate (RPM) | 1000 | 1000 |

TABLE 4-continued

| (Liquid $BF_3$:$H_3PO_4$:$H_2O$ Catalyst) | | |
|---|---|---|
| WHSV Based on Olefin, hr$^{-1}$ | 0.30 | 0.30 |
| Yield | 1.9 | 1.9 |
| (Grams $C_5$+ Alkylate/ Gram Olefin Converted) | | |
| Product Distribution in $C_5$+, wt. % | | |
| $C_5$-$C_7$ | 15.1 | 9.6 |
| $C_8$'s | 70.6 | 78.3 |
| $C_9$+ | 14.3 | 12.1 |
| Ratio of Trimethylpentanes/ Dimethylhexanes in $C_8$'s | 5.1 | 6.2 |

At 168 HOS the catalyst contained a significant amount of polar compounds formed in situ. The yield of $C_5$+ alkylate per gram of 2-butene converted was essentially equivalent (1.9) for fresh and equilibrium $BF_3$:$H_3PO_4$:$H_2O$ catalysts. However, at 168 HOS, the alkylate product contained 78 wt. % $C_8$ paraffins compared to only 70 wt. % $C_8$ paraffins at 72 HOS. This result shows that the equilibrated catalyst, operating in the presence of accumulated polar compounds, is more selective for the primary alkylation products, $C_8$ paraffins.

Changes and modifications in the specifically described embodiments can be carried out without departing from the scope of the invention which is intended to be limited only by the scope of the appended claims.

What is claimed is:

1. An acid catalyst for liquid phase alkylation of an isoparaffin with an olefin comprising a $BF_3$:$H_3PO_4$ adduct, together with at least 31 weight percent of a polar compound formed in situ by reacting an olefin with at least one selected from the group consisting of $H_3PO_4$ and a $BF_3$:$H_3PO_4$ adduct.

2. The acid catalyst of claim 1 wherein said polar compound formed in situ comprises a reaction product of an olefin with a $BF_3$:$H_3PO_4$ adduct.

3. The acid catalyst of claim 1 further comprising from about 4 to about 65 weight percent $BF_3$, from about 2 to about .60 weight percent $H_3PO_4$, and from about 31 to about 90 weight percent of said polar compound.

4. The acid catalyst of claim 3 further comprising up to about 15 weight percent water.

5. The acid catalyst of claim 4 further comprising from about 24 to about 55 weight percent $BF_3$, from about 23 to about 60 weight percent $H_3PO_4$, up to about 7 weight percent water, and from about 31 to about 40 weight percent of said polar compound.

6. The acid catalyst complex of claim 1 further comprising an added solubilizing agent.

7. The acid catalyst of claim 6 wherein said added solubilizing agent comprises a phosphorus-containing ester.

8. The acid catalyst of claim 7 wherein said added solubilizing agent comprises one or more selected from the group consisting of the mono-esters, di-esters, or tri-esters of phosphoric acid.

9. The acid catalyst of claim 6 wherein said added solubilizing agent comprises an anionic or cationic surfactant.

10. The acid catalyst of claim 9 wherein said added solubilizing agent comprises at least one selected from the group consisting of sulfonic and phosphonic compounds.

11. The acid catalyst complex of claim 10 wherein said sulfonic and phosphonic compounds are selected from the group consisting of sulfated esters, sulfated alkanolamides, alkyl sulfates, sulfonates containing aliphatic, aromatic, alkylaromatic or naphthenic constituents, alkylphosphates, alkylpolyphosphates, phosphate mono-esters, phosphate di-esters, and phosphate tri-esters.

* * * * *